US006905522B2

(12) United States Patent
Kravtchenko et al.

(10) Patent No.: US 6,905,522 B2
(45) Date of Patent: Jun. 14, 2005

(54) DYE COMPOSITION COMPRISING AN OXIDATION BASE OF THE DIAMINOPYRAZOLE TYPE, A CATIONIC OXIDATION BASE AND A COUPLER

(75) Inventors: Sylvain Kravtchenko, Asnieres (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 181 days.

(21) Appl. No.: 10/361,579

(22) Filed: Feb. 11, 2003

(65) Prior Publication Data

US 2004/0045100 A1 Mar. 11, 2004
US 2005/0097681 A9 Mar. 11, 2004

Related U.S. Application Data

(60) Provisional application No. 60/372,452, filed on Apr. 16, 2002.

(30) Foreign Application Priority Data

Feb. 12, 2002 (FR) .............................. 02 01713

(51) Int. Cl.$^7$ ................................. A61K 7/13
(52) U.S. Cl. ................ 8/405; 8/406; 8/407; 8/408; 8/410; 8/421; 8/423; 8/470; 8/573; 8/690; 8/692; 548/372.5; 548/373.1
(58) Field of Search ................... 8/405, 406, 407, 8/408, 410, 421, 423, 470, 573, 690, 692; 548/372.5, 373.1

(56) References Cited

U.S. PATENT DOCUMENTS

| 4,003,699 A | | 1/1977 | Rose et al. ................ 8/10.2 |
|---|---|---|---|
| 4,823,985 A | | 4/1989 | Grollier et al. ............ 221/1 |
| 5,061,289 A | | 10/1991 | Clausen et al. ............ 8/405 |
| 5,380,340 A | | 1/1995 | Neunhoeffer et al. ....... 8/409 |
| 5,534,267 A | * | 7/1996 | Neunhoeffer et al. ...... 424/701 |
| 5,663,366 A | * | 9/1997 | Neunhoeffer et al. ... 548/371.4 |
| 5,718,731 A | * | 2/1998 | Loewe et al. ............ 8/409 |
| 5,766,576 A | | 6/1998 | Löwe et al. ............. 424/62 |
| 6,099,592 A | | 8/2000 | Vidal et al. ............. 8/409 |
| 6,270,533 B1 | | 8/2001 | Genet et al. ............. 8/406 |
| 6,340,371 B1 | | 1/2002 | Genet et al. ............. 8/406 |
| 2001/0009044 A1 | | 7/2001 | Braun ................... 8/405 |

FOREIGN PATENT DOCUMENTS

| DE | 23 59 399 | 6/1975 |
|---|---|---|
| DE | 38 43 892 | 6/1990 |
| DE | 41 33 957 | 4/1993 |
| DE | 195 43 988 | 5/1997 |
| DE | 196 43 059 | 4/1998 |
| DE | 196 46 609 | 5/1998 |
| EP | 0 692 245 | 1/1996 |
| EP | 0 770 375 | 5/1997 |
| EP | 0 983 996 | 3/2000 |
| EP | 0 984 007 | 3/2000 |
| FR | 2 586 913 | 3/1987 |
| FR | 2 733 749 | 11/1996 |
| FR | 2 766 177 | 1/1999 |
| FR | 2 801 308 | 5/2001 |
| GB | 1 026 978 | 4/1966 |
| GB | 1153196 | 5/1969 |
| JP | 2-19576 | 1/1990 |
| JP | 5-163124 | 6/1993 |
| WO | WO 94/08970 | 4/1994 |
| WO | WO 99/03819 | 1/1999 |
| WO | WO 99/03836 | 1/1999 |
| WO | WO 00/43367 | 7/2000 |
| WO | WO 00/43396 | 7/2000 |

OTHER PUBLICATIONS

English abstract of the Patent No. DE 29909427U1 filed Jul. 22, 1999.*
English language Derwent Abstract of DE 196 46 609, May 14, 1998.
English language Derwent Abstract of EP 0 770 375, May 2, 1997.
English language Derwent Abstract of EP 0 983 996, Mar. 8, 2000.
English language Derwent Abstract of FR 2 801 308, May 25, 2001.
English language Derwent Abstract of JP 2–19576, Jan. 23, 1990.
English language Derwent Abstract of JP 5–163124, Jun. 29, 1993.
Rudolf Hüttel et al., "Über N–Nitro–pyrazole," Chemische Berichte, vol. 8, No. 9, Jul. 14, 1955, pp. 1586–1591.
K.J. Klebe et al., "A Facile Synthesis of 3(5)–Aminopyrazoles," SYNTHESIS, International Journal of Methods in Synthetic Organic Chemistry, No. 5, May 1973, pp. 294–295.
J.P.H. Juffermans et al., "Selective Thermolysis Reactions of Bromo–1–nitro–1H–pyrazoles. Formation of 3–Nitro–1H–pyrazoles," J. Org. Chem., vol. 51, 1986, pp. 4656–4660.
English language Derwent Abstract of FR 2 766 177, Jan. 22, 1999.

* cited by examiner

Primary Examiner—Mark Kopec
Assistant Examiner—Eisa Elhilo
(74) Attorney, Agent, or Firm—Finnegan, Henderson, Farabow, Garrett & Dunner LLP

(57) ABSTRACT

Dye compositions comprising, in a medium suitable for dyeing:
- at least one first oxidation base chosen from 4,5-diaminopyrazole derivatives of formula (I) and addition salts thereof,
- at least one second cationic oxidation base chosen from monobenzenic, dibenzenic and heterocyclic oxidation bases, and the addition salts thereof, comprising at least one cationic group Z chosen from aliphatic chains optionally bearing at least one ring chosen from saturated and unsaturated rings; wherein said at least one cationic group Z is linked directly to at least one benzenic ring or to at least one heterocycle of said at least one second cationic oxidation base or linked to at least one amine functional group borne by said at least one benzenic ring or said at least one heterocycle; and
- at least one coupler;

as well as the use of this composition for dyeing keratin fibers and the dying process using this composition.

41 Claims, No Drawings

DYE COMPOSITION COMPRISING AN OXIDATION BASE OF THE DIAMINOPYRAZOLE TYPE, A CATIONIC OXIDATION BASE AND A COUPLER

This application claims benefit of U.S. Provisional Application No. 60/372,452, filed Apr. 16, 2002.

The disclosure relates to a dye composition comprising, in a medium suitable for dyeing, at least one first oxidation base of the diaminopyrazole type, at least one second cationic oxidation base chosen from monobenzenic, dibenzenic and heterocyclic oxidation bases and at least one coupler.

It is a well-known practice to dye keratin fibres, such as human hair, with dye compositions comprising oxidation dye precursors, generally known as oxidation bases, such as ortho- or para-phenylenediamines, ortho- or para-aminophenols and heterocyclic compounds. These oxidation bases are colourless or weakly coloured compounds, that, when combined with oxidizing products, may give rise to coloured compounds by a process of oxidative condensation.

It is also well-known that the shades obtained with these oxidation bases may be varied by combining them with couplers or coloration modifiers. The couplers or coloration modifiers may be chosen, for example, from aromatic meta-diamines, meta-aminophenols, meta-diphenols and certain heterocyclic compounds, such as indole compounds.

The variety of molecules used as oxidation bases and couplers make it possible, for example, to obtain a wide range of colours.

The "permanent" coloration obtained by means of these oxidation dyes should moreover satisfy a number of properties. For example, it should have no toxicological drawbacks. It should, further for example, allow shades to be obtained in the desired intensity. And it should, even further for example, show good resistance to external agents such as light, bad weather, washing, permanent waving, perspiration and rubbing.

The oxidation dyes should be able to make it possible, for example, to cover white hair. And the oxidation dyes should also be as unselective as possible, i.e. they should produce the smallest possible colour differences along the same length of keratin fibre, which is generally differently sensitized (i.e. damaged) between its end and its root.

Dye compositions comprising diaminopyrazole derivatives as oxidation bases are already known. For example, Patent Application No. DE 3 843 892 discloses dye compositions for dyeing keratin fibres, comprising 4,5-diaminopyrazole derivatives that may be substituted in position 2 with alkyl or hydroxyalkyl radicals. Patent Application No. EP 692 245 discloses dye compositions comprising 4,5-diaminopyrazole derivatives combined with particular meta-phenylenediamines. Patent Application No. DE 196 43 059 discloses dye compositions combining 4,5-diaminopyrazole derivatives with meta-aminophenol and meta-phenylenediamine couplers. Patent Application No. DE 196 46 609 discloses dye compositions combining 4,5-diaminopyrazole derivatives with benzoxazine couplers.

Dye compositions comprising para-phenylenediamines containing an aliphatic or cyclic cationic group are furthermore known in Patent Application Nos. WO 99/03819 and WO 99/03836.

However, the shades obtained with dye compositions comprising this type of oxidation base may not be, for example, sufficiently strong, chromatic and/or fast.

Accordingly, embodiments of this disclosure provide, for example, novel dye compositions for dyeing keratin fibres, comprising diaminopyrazole derivatives, which can overcome at least one of the drawbacks of the prior art. For example, one embodiment of this disclosure provides dye compositions comprising diaminopyrazole derivatives that may be relatively unselective and particularly fast, while at the same time being capable of generating intense colorations in varied shades.

Disclosed herein is a dye composition comprising, in a medium suitable for dyeing:
at least one first oxidation base chosen from 4,5-diaminopyrazole derivatives of formula (I) and the addition salts thereof,

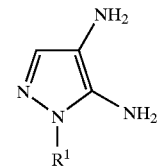

(I)

wherein:
$R^1$ is chosen from $C_1$–$C_6$ alkyl radicals substituted with at least one radical chosen from $OR^2$ radicals wherein $R^2$ is chosen from $C_1$–$C_6$ alkyl radicals;
at least one second cationic oxidation base chosen from monobenzenic, dibenzenic, and heterocyclic oxidation bases, and the addition salts thereof, wherein said at least one second cationic oxidation base comprises at least one cationic group Z chosen from aliphatic chains optionally bearing at least one ring chosen from saturated and unsaturated rings; wherein said at least one cationic group Z is linked directly to at least one benzenic ring or to at least one heterocycle of the said at least one second cationic oxidation base or linked to at least one amine functional group borne by said at least one benzenic ring or said at least one heterocycle; and
at least one coupler.

The composition disclosed herein may, for example, make it possible to obtain at least one of chromatic, very strong, relatively unselective, and fast coloration of keratin fibres.

Further disclosed herein is the use of the composition for dyeing keratin fibres, for example, human keratin fibres such as the hair.

Even further disclosed herein are a dyeing device and a dyeing process using the composition.

As defined herein, the 4,5-diaminopyrazole derivatives of formula (I) further include any corresponding tautomer thereof, where a tautomeric equilibrium exists.

In one embodiment, the at least one first oxidation base is chosen from 4,5 diaminopyrazole derivatives of formula (I) and the addition salts thereof, wherein $R^1$ is chosen from $C_1$–$C_4$ alkyl radicals, for example, $C_2$–$C_4$ alkyl radicals substituted with at least one radical chosen from $OR^2$ radicals, wherein $R^2$ is chosen from $C_1$–$C_4$ alkyl radicals, for example, $C_1$–$C_2$ alkyl radicals. Further, for example, the at least one first oxidation base is chosen from 4,5-diamino-1-(2'-methoxyethyl)pyrazole and the addition salts thereof.

As used herein, the term "alkyl" means linear or branched radicals, for example, methyl, ethyl, n-propyl, isopropyl, butyl, etc. An alkoxy radical is a radical alkyl-O wherein the alkyl radical has the definition given above. The term "halogen" means an entity chosen from, for example, Cl, Br, I and F.

In one embodiment, the at least one second cationic oxidation base is chosen from monobenzenic, dibenzenic, and heterocyclic oxidation bases, and the addition salts thereof, wherein said at least one second cationic oxidation base comprises at least one cationic group Z chosen from aliphatic chains optionally bearing at least one ring chosen from saturated and unsaturated rings; wherein said at least one cationic group Z is linked directly to at least one benzenic ring or to at least one heterocycle of said at least one second cationic oxidation base, or linked to at least one amine functional group borne by said at least one benzenic ring or said heterocycle, and the at least one cationic group Z is chosen, for example, from unsaturated cationic groups of formulae (II) and (III) below, and saturated cationic groups of formula (IV) below:

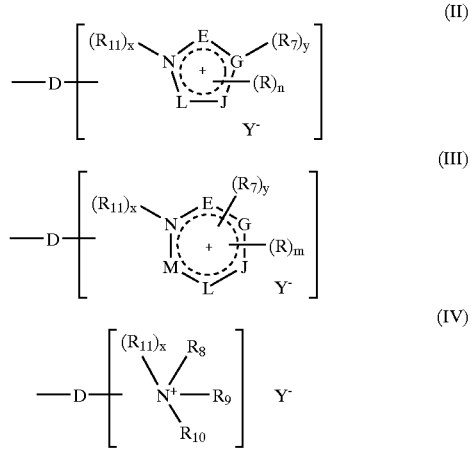

wherein:

D is a linking arm chosen from linear and branched alkylene chains, comprising, for example, from 1 to 14 carbon atoms, which may be interrupted with at least one hetero atom chosen, for example, from oxygen, sulphur and nitrogen atoms, and which may be substituted with at least one radical chosen from hydroxyl and $C_1$–$C_6$ alkoxy radicals, and which may bear at least one ketone functional group;

the ring members E, G, J, L and M, which may be identical or different, are each chosen from carbon, oxygen, sulphur and nitrogen atoms;

n is an integer ranging from 0 to 4;

m is an integer ranging from 0 to 5;

R and $R_7$ to $R_{11}$, which may be identical or different, are each chosen from halogen atoms, a hydroxyl radical, amino groups, cyano groups, amido groups, $SO_3X$ groups, aryl groups, and $Z_1$, $OZ_1$, $NHZ_1$ and $NZ_1Z_2$ radicals; two of the radicals chosen from $R_8$, $R_9$ and $R_{10}$ may form a 5- or 6-membered saturated heterocycle, which may be interrupted with at least one additional hetero atom chosen, for example, from oxygen, sulphur and nitrogen atoms and which may comprise at least one substituent chosen from hydroxyl, amino, halogen, cyano, amido and $CO_2X$ groups, $C_1$–$C_6$ alkyl radicals, $C_1$–$C_6$ alkoxy radicals, $C_1$–$C_6$ monoalkylamino radicals and $C_1$–$C_6$ dialkylamino radicals;

$Z_1$ and $Z_2$, which may be identical or different, are each chosen from linear and branched $C_1$–$C_{14}$ hydrocarbon-based chains, which may be interrupted with at least one hetero atom chosen, for example, from oxygen, sulphur and nitrogen atoms and which may comprise at least one substituent chosen from hydroxyl, amino, amido, halogen, cyano and $CO_2X$ groups, $C_1$–$C_6$ alkyl radicals, $C_1$–$C_6$ alkoxy radicals, $C_1$–$C_6$ monoalkylamino radicals and $C_1$–$C_6$ dialkylamino radicals;

X is chosen from hydrogen, alkali metal and alkaline-earth metal residues, ammonium ions, $C_1$–$C_6$ alkyl radicals and residues derived from an organic amine;

$Y^-$ is an anion chosen from monovalent and divalent anions derived from at least one acid chosen from mineral and organic acids and is, for example, chosen from halogens such as chlorine, bromine, fluorine and iodine, a hydrogen sulphate, and ($C_1$–$C_6$)alkyl sulphates such as methyl sulphate and ethyl sulphate;

x and y are integers equal to 0 or 1; with the following conditions:

in the unsaturated cationic groups of formula (II):

when x=0, the linking arm D is attached to the nitrogen atom of the unsaturated ring, when x=1, the linking arm D is attached to one of the ring members E, G, J or L, y can take the value 1 only:

1) when the ring members E, G, J and L simultaneously are each a carbon atom, and when the radical $R_7$ is borne by the nitrogen atom of the unsaturated ring; or 2) when at least one of the ring members E, G, J and L is a nitrogen atom to which the radical $R_7$ is attached;

in the unsaturated cationic groups of formula (III):

when x=0, the linking arm D is attached to the nitrogen atom of the unsaturated ring, when x=1, the linking arm D is attached to one of the ring members E, G, J, L or M, y can take the value 1 only when at least one of the ring members E, G, J, L and M is a divalent atom, and when the radical $R_7$ is borne by the nitrogen atom of the unsaturated ring;

in the cationic groups of formula (IV):

when x=0, then the linking arm is attached to the nitrogen atom bearing the radicals $R_8$ to $R_{10}$, when x=1, then two of the radicals chosen from $R_8$, $R_9$ and $R_{10}$ form, together with the nitrogen atom to which they are attached, a 5- or 6-membered saturated ring as defined above, and the linking arm D is borne by a carbon atom of said saturated ring.

The unsaturated rings of the groups Z of formula (II) above may be chosen, for example, from pyrrole, imidazole, pyrazole, oxazole, thiazole and triazole rings.

The unsaturated rings of the groups Z of formula (III) above, may be chosen, for example, from pyridine, pyrimidine, pyrazine, oxazine and triazine rings.

The saturated rings of the groups Z of formula (IV) above may be chosen, for example, from pyrrolidine, piperidine, piperazine and morpholine rings.

In one embodiment, the linking arm D is an alkylene chain comprising from 1 to 10 carbon atoms.

The at least one second cationic oxidation base chosen from monobenzenic, dibenzenic and heterocyclic oxidation bases may be optionally substituted on at least one group chosen from benzenic and heterocyclic groups.

The at least one second cationic oxidation base may be chosen, for example, from:

(i) monobenzenic para-phenylenediamines and monobenzenic para-aminophenols, such as those disclosed in European Patent Application Nos. 968 171 and 928 289, which are incorporated herein by reference;

(ii) dibenzenic para-phenylenediamines and dibenzenic para-aminophenols, such as those disclosed in European Patent Application No. 932 602, which is incorporated herein by reference;

(iii) monobenzenic ortho-phenylenediamines, such as those disclosed in European Patent Application Nos. 983 996 and 984 007, which are incorporated herein by reference;

(iv) dibenzenic ortho-phenylenediamines, such as those disclosed in European Patent Application No. 984 006, which is incorporated herein by reference;

(v) heterocyclic oxidation bases of the pyrazole type, such as those disclosed in European Patent Application No. 1 147 090, which is incorporated hereinby reference; and (vi) heterocyclic oxidation bases of the pyrazolo[1,5-a] pyrimidine type, such as those disclosed in European Patent Application 1 147 109, which is incorporated herein by reference.

The monobenzenic para-phenylenediamines and monobenzenic para-aminophenols may be chosen from:

[2-(2,5-diaminophenoxy)ethyl]diethylmethylammonium chloride;
N,N-bis(trimethylammoniumpropyl)-4-aminoaniline dichloride;
[4-(4-aminophenylamino)pentyl]diethylmethylammonium chloride;
[4-(4-aminophenylamino)pentyl]diethyl-(2-hydroxyethyl)ammonium chloride;
[2-(4-aminophenylamino)ethyl]diethylmethylammonium chloride;
{2-[(4-aminophenyl)methylamino]ethyl}trimethylammonium chloride;
[3-(4-aminophenylamino)propyl]trimethylammonium chloride;
[2-(4-aminophenylamino)propyl]trimethylammonium chloride;
[4-(4-amino-2-methylphenylamino)pentyl]diethylmethylammonium chloride;
[4-(4-amino-3-methylphenylamino)pentyl]diethylmethylammonium chloride;
1-{[5-amino-2-(2-hydroxyethylamino)phenylcarbamoyl]methyl}-1,4-dimethylpiperazin-1-ium chloride;
1-[2-(4-aminophenylamino)ethyl]-3-methyl-3H-imidazol-1-ium bromide;
1-[3-(2,5-diaminophenoxy)propyl]-3-methyl-3H-imidazol-1-ium chloride;
3-[3-(4-aminophenylamino)propyl]-1-methyl-3H-imidazol-1-ium chloride;
3-[3-(4-amino-3-methylphenylamino)propyl]-1-methyl-3H-imidazol-1-ium chloride;
3-[3-(4-amino-2-methylphenylamino)propyl]-1-methyl-3H-imidazol-1-ium chloride;
3-[3-(4-amino-2-fluorophenylamino)propyl]-1-methyl-3H-imidazol-1-ium chloride;
3-[3-(4-amino-2-cyanophenylamino)propyl]-1-methyl-3H-imidazol-1-ium chloride;
1-[2-(4-amino-2-methoxyphenylamino)ethyl]-3-methyl-3H-imidazol-1-ium chloride;
1-(5-amino-2-hydroxybenzyl)-3-methyl-3H-imidazol-1-ium chloride;
1-(5-amino-2-hydroxybenzyl)-2-methyl-2H-pyrazol-1-ium chloride;
1-[2-(2,5-diaminophenyl)ethyl]-3-methyl-3H-imidazol-1-ium chloride;
3-[2-(2,5-diaminophenyl)ethyl]-1-methyl-3H-imidazol-1-ium chloride;
1-{2-[(4-aminophenyl)ethylamino]ethyl}-3-methyl-3H-imidazol-1-ium chloride;
N,N-bis[2-(3-methyl-3H-imidazol-1-ium)ethyl]-4-aminoaniline dichloride;
3-[2-(4-aminophenylamino)butyl]-1-methyl-3H-imidazol-1-ium chloride;
1-{[5-amino-2-(2-hydroxyethylamino)phenylcarbamoyl]methyl}-3-methyl-3H-imidazol-1-ium chloride;
4-[2-(2,5-diaminophenoxy)ethyl]-1,3-dimethyl-3H-imidazol-1-ium bromide;
2-(2,5-diaminophenoxymethyl)-1,3-dimethyl-3H-imidazol-1-ium chloride;
4-[3-(4-aminophenylamino)propyl]-1,3-dimethyl-3H-imidazol-1-ium chloride;
4-[3-(4-amino-3-methylphenylamino)propyl]-1,3-dimethyl-3H-imidazol-1-ium chloride;
4-[(2,5-diaminophenylcarbamoyl)methyl]-1,3-dimethyl-3H-imidazol-1-ium chloride;
4-{2-[2-(2-amino-5-hydroxyphenyl)acetylamino]ethyl}-1,3-dimethyl-3H-imidazol-1-ium chloride;
4-[(5-amino-2-hydroxybenzylcarbamoyl)methyl]-1,3-dimethyl-3H-imidazol-1-ium chloride;
and the addition salts thereof.

The monobenzenic para-phenylenediamines and monobenzenic para-aminophenols may, for example, be chosen from:

[2-(2,5-diaminophenoxy)ethyl]diethylmethylammonium chloride;
N,N-bis(trimethylammoniumpropyl)-4-aminoaniline chloride;
[4-(4-aminophenylamino)pentyl]diethylmethylammonium chloride;
[2-(4-aminophenylamino)ethyl]diethylmethylammonium chloride;
{2-[(4-aminophenyl)methylamino]ethyl}trimethylammonium chloride;
[3-(4-aminophenylamino)propyl]trimethylammonium chloride;
[4-(4-aminophenylamino)pentyl]diethyl-(2-hydroxyethyl)ammonium chloride;
3-[3-(4-aminophenylamino)propyl]-1-methyl-3H-imidazol-1-ium chloride;
1-[3-(2,5-diaminophenoxy)propyl]-3-methyl-3H-imidazol-1-ium chloride;
3-[3-(4-amino-3-methylphenylamino)propyl]-1-methyl-3H-imidazol-1-ium chloride;
3-[3-(4-amino-2-methylphenylamino)propyl]-1-methyl-3H-imidazol-1-ium chloride;
1-[2-(4-amino-2-methoxyphenylamino)ethyl]-3-methyl-3H-imidazol-1-ium chloride;
3-[3-(4-amino-2-fluorophenylamino)propyl]-1-methyl-3H-imidazol-1-ium chloride;
3-[3-(4-amino-2-cyanophenylamino)propyl]-1-methyl-3H-imidazol-1-ium chloride and the addition salts thereof.

The dibenzenic para-phenylenediamines and dibenzenic para-aminophenols may be chosen from:

1,3-bis-1{3{3'[(4"-amino-3"-methylaniline)-N-propyl]}-3H-imidazol-1-ium}propane dichloride;
1,3-bis-1{3{3'[(4"-amino-2"-methylaniline)-N-propyl]}-3H-imidazol-1-ium}propane dichloride;
1,3-bis-1{3{3'[(4"-aminoaniline)-N-propyl]}-3H-imidazol-1-ium}propane dichloride;
1,3-bis-1{3{3'[(4"-aminoaniline)-N-propyl]}-3H-imidazol-1-ium}-2-propanol dichloride;
$N_1,N_3$-bis-[3-N-(4'-aminoaniline)propyl]-1,1,3,3-tetramethyl-1,3-diammoniumpropane dibromide;
1,4-bis-1{3[3-(2,5-diaminophenoxy)propyl]-3H-imidazol-1-ium)butane dichloride;
1,3-bis[3-(2,5-diaminophenoxy)propyl]-3H-imidazol-1-ium monochloride;

$N_1,N_4$-bis-[3-N-methyl-N-(4'-aminoaniline)ethyl]-1,1,4,4-tetramethyl-1,3-diammoniumpropane dibromide;

1,4-bis-1-[3-(5-amino-2-hydroxybenzyl)-3H-imidazol-1-ium]butane dichloride;

1,3-bis-{[2-(4-aminoaniline)propyl]-1,1,3,3-tetramethyldiammoniumpropane dibromide;

1,3-bis-{[4-(4-aminoaniline)pentyl]-1,1,3,3-tetramethyldiammoniumpropane dichloride;

[4-(4-aminophenylamino)pentyl]-(5-amino-2-hydroxybenzyl)diethylammonium monochloride;

[2-(4-aminophenylamino)propyl]-(5-amino-2-hydroxybenzyl)dimethylammonium monochloride;

1,3-bis-1-{3-[3-(2,5-diaminophenoxy)propyl]-3H-imidazol-1-ium}propane dichloride;

1,3-bis-1{3{3'[(4"-aminoaniline)-N-propyl]}-3H-imidazol-1-ium}propane dichloride;

1,3-bis-1{4{4'(4-[3-(4"-aminophenylamino)propyl]}-1,3-dimethyl-3H-imidazol-1-ium}propane dichloride;

1,3-bis-1{4{4'(4-[3-(4"-amino-2"-methylaniline)propyl]}-1,3-dimethyl-3H-imidazol-1-ium}propane dichloride;

4-[2-(2,5-diaminophenoxy)ethyl]-3-[3-(2,5-diaminophenoxy)propyl]-1-methyl-3-imidazol-1-ium monochloride;

4-[2-(2,5-diaminophenoxy)ethyl]-1-[3-(2,5-diaminophenoxy)propyl]-3-methyl-3-imidazol-1-ium monochloride;

and the addition salts thereof.

The dibenzenic para-phenylenediamines and dibenzenic para-aminophenols may be chosen, for example, from:

1,3-bis-1{3{3'[(4"-aminoaniline)-N-propyl]}-3H-imidazol-1-ium}propane dichloride;

1,3-bis[3-(2,5-diaminophenoxy)propyl]-3H-imidazol-1-ium monochloride;

$N_1,N_4$-bis-[3-N-methyl-N-(4'-aminoaniline)ethyl]-1,1,4,4-tetramethyl-1,3-diammoniumpropane dibromide;

1,4-bis-1-[3-(5-amino-2-hydroxybenzyl)-3H-imidazol-1-ium]butane dichloride;

1,3-bis-1{3{3'[(4"-aminoaniline)-N-propyl]}-3H-imidazol-1-ium}propane dichloride;

and the addition salts thereof.

The monobenzenic ortho-phenylenediamines may be chosen from:

{2-[2-aminophenylamino]ethyl}trimethylammonium monochloride;

[2-(2-amino-5-chlorophenylamino)ethyl]trimethylammonium monochloride;

[2-(2-amino-6-chlorophenylamino)ethyl]trimethylammonium monochloride;

[2-(2-amino-4-chlorophenylamino)ethyl]trimethylammonium monochloride;

{2-[2-amino-4-chloro-5-(2-hydroxyethoxy)phenylamino]ethyl}trimethylammonium monochloride;

[2-(2-amino-5-methoxyphenylamino)ethyl]trimethylammonium monochloride;

[2-(2-aminophenylamino)ethyl]-(2-hydroxyethyl)dimethylammonium monobromide;

4-[2-(2-aminophenylamino)ethyl]-4-methylmorpholin-4-ium monochloride;

1-[2-(2-aminophenylamino)ethyl]-1-ethylpiperidinium monochloride;

1-[2-(2-aminophenylamino)ethyl]-1,4-dimethylpiperazin-1-ium monochloride;

4-[2-(1-methylpiperidinium)ethoxy]N-2-[2-(1-methylpiperidinium)ethyl]benzene-1,2-diamine dichloride;

1-[2-(2-amino-5-methylsulphanylphenylamino)ethyl]-1-methylpiperidinium monochloride;

1-[2-(2-aminophenylamino)ethyl]-1-methylpyrrolidinium monochloride;

[3-(2-aminophenylamino)propyl]diethylmethylammonium monochloride;

N,N'-bis-[2-(1-methylpiperidinium)ethyl]benzene-1,2-diamine dichloride;

[2-(2-amino-4-methylphenylamino)ethyl]trimethyl [lacuna] monochloride;

3-[3-(2-aminophenylamino)propyl]-1-methyl-3H-imidazol-1-ium monochloride;

3-[2-(2-aminophenylamino)ethyl]-1-methyl-3H-imidazol-1-ium monochloride;

4-[2-(1-methyl-3H-imidazol-1-ium)ethoxy]-N2-[2-(1-methyl-3H-imidazol-1-ium)ethyl]benzene-1,2-diamine dichloride;

3-[2-(2-amino-4-methylphenylamino)ethyl]-1-ethyl-3H-imidazol-1-ium monochloride;

3-[3-(2-aminophenylamino)propyl]-1-(3-trimethylammonium-2-hydroxypropyl)-3H-imidazol-1-ium dichloride;

3-[3-(2-aminophenylamino)propyl]-1-(2-hydroxyethyl)-3H-imidazol-1-ium monobromide;

3-{[2-(2-aminophenylamino)ethylcarbamoyl]methyl}-1-methyl-3H-imidazol-1-ium monochloride;

1-[2-(2-amino-4-chlorophenylamino)ethyl]pyridinium monochloride;

3-[2-(2-amino-5-methoxyphenylamino)ethyl]-1-methyl-3H-imidazol-1-ium monochloride;

3-[2-(2-amino-5-methylsulphanylphenylamino)ethyl]-1-methyl-3H-imidazol-1-ium monochloride;

and the addition salts thereof.

The monobenzenic ortho-phenylenediamines may be chosen, for example, from:

{2-[2-aminophenylamino]ethyl}trimethylammonium chloride;

3-[3-(2-aminophenylamino)propyl]-1-methyl-3H-imidazol-1-ium chloride;

and the addition salts thereof.

The dibenzenic ortho-phenylenediamines may be chosen from:

1,3-bis-{3-{3-[(2-aminoaniline)-N-propyl]}-3H-imidazol-1-ium}propane dibromide;

$N_1,N_3$-bis-[3-N-(2-aminoaniline)propyl]-1,1,3,3-tetramethyl-1,3-diammoniumpropane dibromide;

1,4-bis-{3-{2-[(2-aminoaniline)-N-ethyl]}-3H-imidazol-1-ium}butane dichloride;

1-[2-(2-aminoaniline)ethyl]-3-[3-(2-aminoaniline)propyl]-3H-imidazol-1-ium monochloride;

and the addition salts thereof.

The dibenzenic ortho-phenylenediamines may, for example, be chosen from:

1,3-bis-1-{3-{3-[(2-aminoaniline)-N-propyl]}-3H-imidazol-1-ium}propane dibromide;

$N_1,N_3$-bis-[3-N-(2-aminoaniline)propyl]-1,1,3,3-tetramethyl-1,3-diammoniumpropane dibromide; and the addition salts thereof.

The heterocyclic oxidation bases of the pyrazole type may be chosen from:

[3-(4-amino-2,5-dimethyl-2H-pyrazol-3-ylamino)propyl]trimethylammonium chloride;

[3-(4-amino-2,5-dimethyl-2H-pyrazol-3-ylamino)propyl]-(2-hydroxyethyl)dimethylammonium chloride;

3-[3-(4-amino-2,5-dimethyl-2H-pyrazol-3-ylamino)propyl]-1-(2-hydroxyethyl)-3H-imidazol-1-ium chloride;

3-[(4-amino-2H-pyrazol-3-ylcarbamoyl)methyl]-1-methyl-3H-imidazol-1-ium chloride;

3-[2-(4,5-diamino-3-methylpyrazol-1-yl)ethyl]-1-methyl-3H-imidazol-1-ium chloride;

3-[2-(4,5-diaminopyrazol-1-yl)ethyl]-1-methyl-3H-imidazol-1-ium chloride;
[2-(4,5-diamino-3-methylpyrazol-1-yl)ethyl]trimethylammonium chloride;
[2-(4,5-diaminopyrazol-1-yl)ethyl]trimethylammonium chloride;
[2-(4-amino-5-hydroxypyrazol-1-yl)ethyl]trimethylammonium chloride;
[2-(4-amino-5-hydroxy-3-methylpyrazol-1-yl)ethyl]trimethylammonium chloride;
3-[2-(4-amino-5-hydroxy-3-methylpyrazol-1-yl)ethyl]-1-methyl-3H-imidazol-1-ium chloride;
3-[2-(4-amino-5-hydroxypyrazol-1-yl)ethyl]-1-methyl-3H-imidazol-1-ium chloride;
3-[2-(4,5-diamino-1-methyl-1H-pyrazol-3-yl)ethyl]-1-methyl-3H-imidazol-1-ium chloride;
and the addition salts thereof, and the possible tautomeric forms thereof.

The heterocyclic oxidation bases of the pyrazole type may be chosen, for example, from:
[3-(4-amino-2,5-dimethyl-2H-pyrazol-3-ylamino)propyl] trimethylammonium chloride;
[3-(4-amino-2,5-dimethyl-2H-pyrazol-3-ylamino)propyl]-(2-hydroxyethyl)dimethylammonium chloride;
3-[3-(4-amino-2,5-dimethyl-2H-pyrazol-3-ylamino) propyl]-1-(2-hydroxyethyl)-3H-imidazol-1-ium chloride;
3-[(4-amino-2H-pyrazol-3-ylcarbamoyl)methyl]-1-methyl-3H-imidazol-1-ium chloride;
3-[2-(4,5-diamino-3-methylpyrazol-1-yl)ethyl]-1-methyl-3H-imidazol-1-ium chloride;
3-[2-(4,5-diamino-1-methyl-1H-pyrazol-3-yl)ethyl]-1-methyl-3H-imidazol-1-ium chloride,
and the addition salts thereof, and the possible tautomeric forms thereof.

The heterocyclic oxidation bases of the pyrazolo[1,5-a] pyrimidine type may be chosen from:
1-[3-(3-amino-5,6-dimethylpyrazolo[1,5-a]pyrimidin-7-ylamino)propyl]-3-methyl-3H-imidazol-1-ium monobromide,
3-[3-(3-amino-5-methylpyrazolo[1,5-a]pyrimidin-7-ylamino)propyl]-1-(2-hydroxyethyl)-3H-imidazol-1-ium chloride,
3-[(3-aminopyrazolo[1,5-a]pyrimidin-7-ylcarbamoyl) methyl]-1-methyl-3H-imidazol-1-ium chloride,
3-(3-amino-7-hydroxy-5-methylpyrazolo[1,5-a]pyrimidin-6-ylmethyl)-1-methylpyridinium methyl sulphate,
3-(3-amino-7-hydroxy-5-methylpyrazolo[1,5-a]pyrimidin-6-ylmethyl)-1-(2-hydroxyethyl)pyridinium chloride,
2-[(3-aminopyrazolo[1,5-a]pyrimidin-7-ylamino)methyl]-1,3-dimethyl-3H-imidazol-1-ium methyl sulphate,
3-[(3-aminopyrazolo[1,5-a]pyrimidin-7-ylamino)methyl]-1-methylpyridinium methyl sulphate,
3-[(3-aminopyrazolo[1,5-a]pyrimidin-7-ylamino)methyl]-1-methylpyridinium methyl sulphate,
2-(3,7-diamino-5-methylpyrazolo[1,5-a]pyrimidin-6-ylmethyl]-1,3-dimethyl-3H-imidazol-1-ium methyl sulphate,
2-(3-amino-7-hydroxy-5-methylpyrazolo[1,5-a]pyrimidin-6-ylmethyl)-1,3-dimethyl-3H-imidazol-1-ium methyl sulphate,
2-(3,7-diaminopyrazolo[1,5-a]pyrimidin-2-yl)-1-methylpyridinium methyl sulphate,
[3-(3-amino-5-methylpyrazolo[1,5-a]pyrimidin-7-ylamino) propyl]trimethylammonium chloride,
[3-(3-amino-5-methylpyrazolo[1,5-a]pyrimidin-7-ylamino) propyl]trimethylammonium methyl sulphate,
1-[3-(3-amino-5-methylpyrazolo[1,5-a]pyrimidin-7-ylamino)propyl]-1-methylpiperidinium chloride,
1-[3-(3-amino-5-methylpyrazolo[1,5-a]pyrimidin-7-ylamino)propyl]-1-methylpiperidinium methyl sulphate,
4-[3-(3-amino-5-methylpyrazolo[1,5-a]pyrimidin-7-ylamino)propyl]-4-methylmorpholin-4-ium chloride,
4-[3-(3-amino-5-methylpyrazolo[1,5-a]pyrimidin-7-ylamino)propyl]-4-methylmorpholin-4-ium methyl sulphate,
and the addition salts thereof.

The heterocyclic oxidation bases of the pyrazolo[1,5-a] pyrimidine type may, for example, be chosen from:
1-[3-(3-amino-5,6-dimethylpyrazolo[1,5-a]pyrimidin-7-ylamino)propyl]-3-methyl-3H-imidazol-1-ium monobromide,
3-[3-(3-amino-5-methylpyrazolo[1,5-a]pyrimidin-7-ylamino)propyl]-1-(2-hydroxyethyl)-3H-imidazol-1-ium chloride,
3-(3-amino-7-hydroxy-5-methylpyrazolo[1,5-a]pyrimidin-6-ylmethyl)-1-methylpyridinium methyl sulphate,
3-(3-amino-7-hydroxy-5-methylpyrazolo[1,5-a]pyrimidin-6-ylmethyl)-1-(2-hydroxyethyl)pyridinium chloride,
3-(3-amino-7-hydroxy-5-methylpyrazolo[1,5-a]pyrimidin-6-ylmethyl)-1-methylpyridinium chloride,
4-[3-(3-amino-5-methylpyrazolo[1,5-a]pyrimidin-7-ylamino)propyl]-4-methylmorpholin-4-ium chloride,
4-[3-(3-amino-5-methylpyrazolo[1,5-a]pyrimidin-7-ylamino)propyl]-4-methylmorpholin-4-ium methyl sulphate,
and the addition salts thereof.

The at least one second cationic oxidation base chosen from monobenzenic para-phenylenediamines such as 1,3-bis[3-(2,5-diaminophenoxy)propyl]-3H-imidazol-1-ium monochloride tetrahydrochloride monohydrate may also be used.

The at least one coupler used in the composition disclosed herein may be chosen from couplers conventionally used in the field of dyeing. The at least one coupler may be chosen, for example, from meta-phenylenediamines, meta-aminophenols, meta-diphenols, naphthalenic couplers and heterocyclic couplers, and the addition salts thereof.

The at least one coupler may be chosen, for example, from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino) toluene and the addition salts thereof.

In one embodiment, the at least one coupler may be present in an amount ranging from 0.001% to 10% by weight, relative to the total weight of the dye composition, such as from 0.005% to 6% by weight, relative to the total weight of the dye composition.

The composition disclosed herein may, for example, further comprise at least one additional non-cationic oxidation base chosen from those conventionally used in oxidation dyeing, other than the at least one first oxidation base chosen from 4,5-diaminopyrazole derivatives of formula (I) disclosed above. The at least one additional non-cationic oxidation base may be chosen, for example, from para-phenylenediamines other than those described above, bis(phenyl)alkylenediamines, para-aminophenols, ortho-aminophenols, heterocyclic bases other than those described above, and the addition salts thereof.

The para-phenylenediamines other than those described above may be chosen, for example, from para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-thienyl-para-phenylenediamine and 2-β-hydroxyethylamino-5-aminotoluene, and the addition salts thereof.

The para-phenylenediamines may also be chosen, for example, from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the addition salts thereof, such as acid addition salts thereof.

The bis(phenyl)alkylenediamines may be chosen, for example, from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the addition salts thereof.

The para-aminophenols may be chosen, for example, from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminbmethyl)phenol, 4-amino-2-fluorophenol, and the addition salts thereof.

The ortho-aminophenols may be chosen, for example, from 2-aminophenol, 2-amino-5-methylphenol, 2-amino-6-methylphenol, 5-acetamido-2-aminophenol, and the addition salts thereof.

The heterocyclic bases, other than those described above, may be chosen, for example, from pyridine derivatives, pyrimidine derivatives and pyrazole derivatives, other than those described above.

The pyridine derivatives may be chosen, for example, from the compounds disclosed in Patent Nos. GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the addition salts thereof.

Other pyridine oxidation bases may be chosen, for example, from 3-aminopyrazolo[1,5-a]pyridine oxidation bases and the addition salts thereof disclosed, for example, in patent application FR 2 801 308, such as, for example, pyridine oxidation bases chosen from pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol and the addition salts thereof.

The pyrimidine derivatives may be chosen, for example, from the compounds disclosed, for example, in Patent Nos. DE 2 359 399, JP 88-169 571; JP 05 163 124; and EP 0 770 375; and Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives which may be chosen, for example, from those disclosed in Patent Application No. FR-A-2 750 048, such as pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylamino-pyrazolo[1,5-a]pyrimidine, and the addition salts thereof and the tautomeric forms thereof, where a tautomeric equilibrium exists.

The pyrazole derivatives may be chosen, for example, from the compounds disclosed in Patent Nos. DE 3 843 892 and DE 4 133 957 and Patent Application Nos. WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

The oxidation bases present in the composition may each present in an amount ranging, for example, from 0.001% to 10% by weight, relative to the total weight of the dye composition, such as from 0.005% to 6% by weight, relative to the total weight of the dye composition.

The addition salts of the oxidation bases and of the at least one coupler may be chosen, for example, from the acid addition salts, such as hydrochlorides, hydrobromides, sulphates, citrates, succinates, tartrates, lactates, tosylates, benzenesulphonates, phosphates and acetates; and the base addition salts, such as sodium hydroxide, potassium hydroxide, ammonia, amines and alkanolamines.

In one embodiment, the dyeing composition may also comprise at least one direct dye chosen, for example, from nitrobenzene dyes, azo direct dyes and methine direct dyes. The at least one direct dye may be of nonionic, anionic or cationic nature.

The medium suitable for dyeing, also known as the dye support, may be chosen, for example, from water and mixtures of water and at least one organic solvent to dissolve the compounds which may not be sufficiently soluble in water. The at least one organic solvent may be chosen, for example, from $C_1$–$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, and aromatic alcohols such as benzyl alcohol and phenoxyethanol.

The at least one organic solvent may be present in an amount ranging, for example, from 1% to 40% by weight, relative to the total weight of the dye composition, such as from 5% to 30% by weight, relative to the total weight of the dye composition.

The dye composition may further comprise at least one adjuvant chosen from adjuvants conventionally used in compositions for dyeing the hair, for example, anionic, cationic, nonionic, amphoteric and zwitterionic surfactants, anionic, cationic, nonionic, amphoteric and zwitterionic polymers, inorganic and organic thickeners, and for example, anionic, cationic, nonionic and amphoteric associative polymeric thickeners, antioxidants, penetration agents, sequestering agents, fragrances, buffers, dispersing agents, packaging agents such as volatile and non-volatile, modified and unmodified silicones, film-forming agents, ceramides, preserving agents and opacifiers.

The at least one adjuvant may be present in an amount ranging, for example, from 0.01% to 20% by weight, relative to the weight of the composition.

Needless to say, a person skilled in the art will take care to select at least one optional additional compound such that the advantageous properties intrinsically associated with the oxidation dye composition disclosed herein are not, or are not substantially, adversely affected by the addition envisaged.

The pH of the dye composition may, for example, range from 3 to 12, such as from 5 to 11. The pH may be adjusted, for example, to the desired value using at least one entity chosen from acidifying and basifying agents usually used in the dyeing of keratin fibres and standard buffer systems.

The acidifying agents may be chosen, for example, from inorganic and organic acids such as hydrochloric acid, orthophosphoric acid, sulphuric acid, carboxylic acids such as acetic acid, tartaric acid, citric acid and lactic acid, and sulphonic acids.

The basifying agents may be chosen, for example, from aqueous ammonia, alkaline carbonates, alkanolamines, such as mono-, di- and triethanolamines and derivatives thereof, sodium hydroxide, potassium hydroxide and the compounds of formula (V) below:

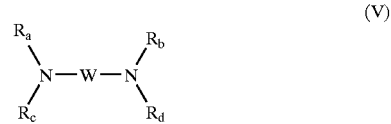

(V)

wherein W is chosen from propylene residues optionally substituted with at least one radical chosen from a hydroxyl radical and $C_1$–$C_4$ alkyl radicals; $R_a$, $R_b$, $R_c$ and $R_d$, which may be identical or different, are each chosen from hydrogen, $C_1$–$C_4$ alkyl radicals and $C_1$–$C_4$ hydroxyalkyl radicals.

The dye composition disclosed herein may be in various forms, such as in a form chosen from liquids, creams and gels, and any other form that is suitable for dyeing keratin fibres, such as human hair.

Further disclosed herein is a dyeing process, comprising applying the dyeing composition disclosed herein to keratin fibres. And the colour may be developed using at least one oxidizing agent. The colour may be developed at acidic, neutral or alkaline pH. The at least one oxidizing agent may be mixed with the dyeing composition disclosed herein at the time of use, or an oxidizing composition comprising the at least one oxidizing agent may be applied simultaneously or sequentially to the dyeing composition disclosed herein.

In one embodiment, the dyeing composition may be mixed, for example, at the time of use, with an oxidizing composition comprising, in a medium suitable for dyeing, at least one oxidizing agent, wherein the at least one oxidizing agent is present in an amount that is sufficient to develop a coloration. The mixture obtained may then be applied to the keratin fibres. After an action time ranging from 3 to 50 minutes, for example, 5 to 30 minutes, the keratin fibres may be rinsed, washed with shampoo, rinsed again, and then dried.

The at least one oxidizing agent may be chosen, for example, from oxidizing agents conventionally used for the oxidation dyeing of keratin fibres, for example, hydrogen peroxide, urea peroxide, alkali metal bromates, persalts such as perborates and persulphates, peracids and oxidase enzymes, such as peroxidases, 2-electron oxidoreductases such as uricases, and 4-electron oxygenases, such as laccases. In one embodiment, the at least one oxidizing agent is hydrogen peroxide.

The oxidizing composition may further comprise, for example, at least one adjuvant chosen, for example, from adjuvants conventionally used in compositions for dyeing the hair, such as those defined above for the dye composition.

The pH of the oxidizing composition comprising the at least one oxidizing agent may be, for example, such that after mixing with the dye composition, the pH of the resulting composition applied to the keratin fibres ranges from 3 to 12, such as from 5 to 11. The pH may be adjusted to the desired value, for example, by using at least one entity chosen from acidifying agents and basifying agents usually used in the dyeing of keratin fibres, and standard buffer systems as defined above.

The ready-to-use composition that is finally applied to the keratin fibres may be in various forms, such as in a form chosen from liquids, creams and gels and any other form that is suitable for dyeing keratin fibres, such as human hair.

Further disclosed herein is a multi-compartment dyeing device or "kit", wherein a first compartment comprises the dye composition disclosed herein and a second compartment comprises an oxidizing composition. This device may be equipped, for example, with a means for applying the desired mixture to the hair, such as the devices disclosed in French Patent No. FR-2 586 913.

The diaminopyrazole compounds that are useful in the dye composition disclosed herein are known compounds that may be obtained, for example, using general preparation processes known to those skilled in the art. For example, the synthetic approach shown below is disclosed in the literature up to the intermediate (2) (J. H. P. Juffermanns, C. L; Habraken; J. Org. Chem. 1986, 51, 4656; Klebe et al.; Synthesis, 1973, 294; R. Hüttel, F. Büchele; Chem. Ber.; 1955, 88, 1586). In the present case, the conversion of intermediate 3 into intermediate 4 is performed using a $R_2NH_2$/EtOH mixture.

The alkylation and the amination to obtain the 4,5-diaminopyrazole derivatives of formula (1) are disclosed in document DE 42 34 885.

The examples that follow illustrate embodiments of the present disclosure without, however, being limiting in nature.

EXAMPLES

Example 1

Synthesis of 4,5-diamino-1-(2'-methoxyethyl)pyrazole dihydrochloride

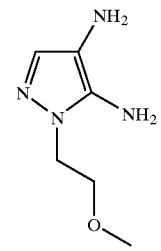

A mixture of 5-benzylamino-3-bromo-1-(2'-methoxyethyl)-4-nitropyrazole (4 g, 2.8 mmol) in ethanol (500 ml) comprising a 10% Pd/C catalyst (Johnson-Mattey Type 487, dry weight 0.5 g) and 36% hydrochloric acid (0.57 g, 5.6 mmol) was hydrogenated in a Parr Autoclave (1 l) at 1 MPa for 1 hour. The catalyst was then removed by filtration and washed with ethanol, and the filtrate was evaporated under reduced pressure. A crude orange-colored solid (2.8 g) was thus obtained, and was triturated in EtOAc (20 ml) for 1 hour. The solid was then filtered off and washed with cold EtOAc (20 ml) and then dried under vacuum to give the 4,5-diamino-1-(2'-methoxyethyl)pyrazole in the form of a beige-colored solid (0.7 g, 27%).

HPLC (purity): 99.5% m.p.: 168.1–173.0° C.

$^1$H NMR: (400 MHz, d$^6$-DMSO): 7.34 (1H, s, NH$_{arom}$), 5.18 (1H, S$_{broad}$, NH), 4.09 (2H, t, J=5.5 Hz, CH$_2$N), 3.61 (2H, t, J=5.5 Hz, CH$_2$O), 3.23 (3H, s, OCH$_3$).

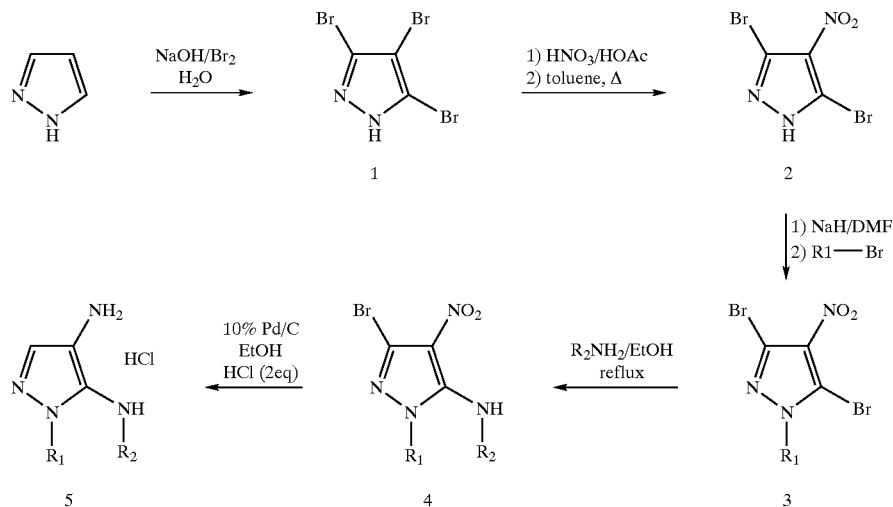

Example 2

Dye composition comprising 4,5-diamino-1-(2'-methoxyethyl)pyrazole hydrochloride The following dye composition was prepared:

| Example | 2 |
|---|---|
| 4,5-Diamino-1-(2'-methoxyethyl)pyrazole 2HCl | $6 \times 10^{-3}$ mol |
| 1,3-Bis[3-(2,5-diaminophenoxy)propyl]-3H-imidazol-1-ium monochloride tetrahydrochloride monohydrate (oxidation base) | $2 \times 10^{-3}$ mol |
| 2-Methyl-5-aminophenol (coupler) | $8 \times 10^{-3}$ mol |
| Dye support | (*) |
| Demineralized water q.s. | 100 g |
| (*) Common dye support | |
| Benzyl alcohol | 2 g |
| Polyethylene glycol 8 EO | 3 g |
| Ethanol | 18 g |
| (C8–C10)alkyl polyglucoside as an aqueous solution comprising 60% active material buffered with ammonium citrate, sold under the name Oramix CG110 by SEPPIC | 5 g in this case |
| Ammonia at 20% $NH_3$ | 10 g |
| Sodium metabisulphite | 0.205 g |
| Sequestering agent | q.s |

At the time of use, the composition was mixed with an equal weight of 20-volumes aqueous hydrogen peroxide solution (6% by weight).

The mixture obtained was applied to locks of natural and permanent-waved grey hair containing 90% white hairs, at a rate of 10 g per 1 g of hair. After an action time of 30 minutes, the locks were rinsed, washed with a standard shampoo, rinsed again, and then dried.

The locks were assessed visually. An intense coppery mahogany coloration was thus obtained.

What is claimed is:

1. A dye composition comprising, in a medium suitable for dyeing:
    at least one first oxidation base chosen from 4,5-diaminopyrazole derivatives of formula (I) and the addition salts thereof,

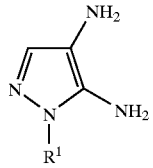

(I)

wherein $R^1$ is chosen from $C_1$–$C_6$ alkyl radicals substituted with at least one radical chosen from $OR^2$ radicals wherein $R^2$ is chosen from $C_1$–$C_6$ alkyl radicals;
    at least one second cationic oxidation base chosen from monobenzenic, dibenzenic and heterocyclic oxidation bases, and the addition salts thereof, wherein said at least one second cationic oxidation base comprises at least one cationic group Z chosen from aliphatic chains optionally bearing at least one ring chosen from saturated and unsaturated rings; wherein said at least one cationic group Z is linked directly to at least one benzenic ring or to at least one heterocycle of said at least one second cationic oxidation base or linked to at least one amine functional group borne by said at least one benzenic ring or said at least one heterocycle; and at least one coupler.

2. The composition according to claim 1, wherein, in defining the at least one first oxidation base chosen from 4,5-diaminopyrazole derivatives of formula (I), $R^1$ is chosen from $C_1$–$C_4$ alkyl radicals substituted with at least one radical chosen from $OR^2$ radicals, wherein $R^2$ is chosen from $C_1$–$C_4$ alkyl radicals.

3. The composition according to claim 2, wherein the at least one first oxidation base is chosen from 4,5-diamino-1-(2'-methoxyethyl)pyrazole and the addition salts thereof.

4. The composition according to claim 1, wherein the at least one cationic group Z is chosen from unsaturated cationic groups of formulae (II) and (III) below, and saturated cationic groups of formula (IV) below:

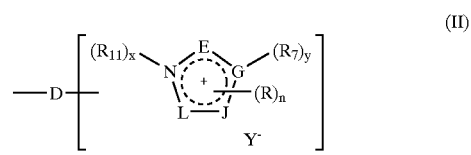

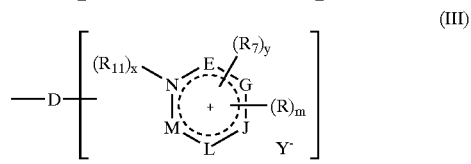

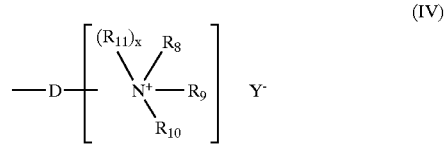

wherein:
D is a linking arm chosen from linear and branched alkylene chains comprising from 1 to 14 carbon atoms, which may be interrupted with at least one hetero atom, and which may be substituted with at least one radical chosen from hydroxyl and $C_1$–$C_6$ alkoxy radicals, and which may bear at least one ketone functional group;
the ring members E, G, J, L and M, which may be identical or different, are each chosen from carbon, oxygen, sulphur and nitrogen atoms;
n is an integer ranging from 0 to 4;
m is an integer ranging from 0 to 5;
R and $R_7$ to $R_{11}$, which may be identical or different, are each chosen from halogen atoms, a hydroxyl radical, amino groups, cyano groups, amido groups, $SO_3X$ groups, aryl groups, and $Z_1$, $OZ_1$, $NHZ_1$, and $NZ_1Z_2$ radicals; two of the radicals chosen from $R_8$, $R_9$, and $R_{10}$ may form a 5- or 6-membered saturated heterocycle, which may be interrupted with at least one additional hetero atom and which may comprise at least one substituent chosen from hydroxyl, amino, halogen, cyano, amido and $CO_2X$ groups, $C_1$–$C_6$ alkyl radicals, $C_1$–$C_6$ alkoxy radicals, $C_1$–$C_6$ monoalkylamino radicals and $C_1$–$C_6$ dialkylamino radicals;
$Z_1$ and $Z_2$, which may be identical or different, are each chosen from linear and branched $C_1$–$C_{14}$ hydrocarbon-based chains, which may be interrupted with at least one hetero atom and which may comprise at least one substituent chosen from hydroxyl, amino, amido, halogen, cyano and $CO_2X$ groups, $C_1$–$C_6$ alkyl radicals, $C_1$–$C_6$ alkoxy radicals, $C_1$–$C_6$ monoalkylamino radicals and $C_1$–$C_6$ dialkylamino radicals;
X is chosen from hydrogen, alkali metal and alkaline-earth metal residues, ammonium ions, $C_1$–$C_6$ alkyl radicals and residues derived from an organic amine;

$Y^-$ is an anion chosen from monovalent and divalent anions derived from at least one acid chosen from mineral and organic acids;

x and y are integers equal to 0 or 1; with the following conditions:

in the unsaturated cationic groups of formula (II):
  when x=0, the linking arm D is attached to the nitrogen atom of the unsaturated ring,
  when x=1, the linking arm D is attached to one of the ring members E, G, J or L,
  y can take the value 1 only:
1) when the ring members E, G, J and L simultaneously are each a carbon atom, and when the radical $R_7$ is borne by the nitrogen atom of the unsaturated ring; or
2) when at least one of the ring members E, G, J and L is a nitrogen atom to which the radical $R_7$ is attached;

in the unsaturated cationic groups of formula (III):
  when x=0, the linking arm D is attached to the nitrogen atom of the unsaturated ring,
  when x=1, the linking arm D is attached to one of the ring members E, G, J, L or M,
  y can take the value 1 only when at least one of the ring members E, G, J, L and M is a divalent atom, and when the radical $R_7$ is borne by the nitrogen atom of the unsaturated ring;

in the cationic groups of formula (IV):
  when x=0, then the linking arm is attached to the nitrogen atom bearing the radicals $R_8$ to $R_{10}$,
  when x=1, then two of the radicals chosen from $R_8$, $R_9$, and $R_{10}$ form, together with the nitrogen atom to which they are attached, a 5- or 6-membered saturated ring, which may be optionally interrupted with at least one additional hetero atom and which may comprise at least one substituent chosen from hydroxyl, amino, halogen, cyano, amido and $CO_2X$ groups, $C_1-C_6$ alkyl radicals, $C_1-C_6$ alkoxy radicals, $C_1-C_6$ monoalkylamino radicals and $C_1-C_6$ dialkylamino radicals, and the linking arm D is borne by a carbon atom of said saturated ring.

5. The composition according to claim 4, wherein the $Y^-$ is an anion chosen from halogens, a hydrogen sulphate, and ($C_1-C_6$)alkyl sulphates.

6. The composition according to claim 5, wherein the halogens are chosen from chlorine, bromine, fluorine, and iodine.

7. The composition according to claim 5, wherein the ($C_1-C_6$)alkyl sulphates are chosen from methyl sulphate and ethyl sulphate.

8. The composition according to claim 4, wherein the at least one hetero atom and the at least one additional hetero atom are chosen from oxygen, sulphur and nitrogen atoms.

9. The composition according to claim 4, wherein the unsaturated ring of the at least one cationic group Z of formula (II) is chosen from pyrrole, imidazole, pyrazole, oxazole, thiazole and triazole rings.

10. The composition according to claim 4, wherein the unsaturated ring of the at least one cationic group Z of formula (III) is chosen from pyridine, pyrimidine, pyrazine, oxazine and triazine rings.

11. The composition according to claim 4, wherein the saturated ring of the at least one cationic group Z of formula (IV) is chosen from pyrrolidine, piperidine, piperazine and morpholine rings.

12. The composition according to claim 4, wherein the linking arm D is an alkylene chain comprising from 1 to 10 carbon atoms.

13. The composition according to claim 1, wherein the at least one second cationic oxidation base is chosen from:

(i) monobenzenic para-phenylenediamines and monobenzenic para-aminophenols;
(ii) dibenzenic para-phenylenediamines and dibenzenic para-aminophenols;
(iii) monobenzenic ortho-phenylenediamines;
(iv) dibenzenic ortho-phenylenediamines;
(v) heterocyclic oxidation bases of the pyrazole type; and
(vi) heterocyclic oxidation bases of the pyrazolo[1,5-a] pyrimidine type.

14. The composition according to claim 13, wherein the monobenzenic para-phenylenediamines and monobenzenic para-aminophenols are chosen from:

[2-(2,5-diaminophenoxy)ethyl]diethylmethylammonium chloride;

N,N-bis(trimethylammoniumpropyl)-4-aminoaniline dichloride;

[4-(4-aminophenylamino)pentyl]diethylmethylammonium chloride;

[4-(4-aminophenylamino)pentyl]diethyl-(2-hydroxyethyl)ammonium chloride;

[2-(4-aminophenylamino)ethyl]diethylmethylammonium chloride;

{2-[(4-aminophenyl)methylamino]ethyl}trimethylammonium chloride;

[3-(4-aminophenylamino)propyl]trimethylammonium chloride;

[2-(4-aminophenylamino)propyl]trimethylammonium chloride;

[4-(4-amino-2-methylphenylamino)pentyl]diethylmethylammonium chloride;

[4-(4-amino-3-methylphenylamino)pentyl]diethylmethylammonium chloride;

1-{[5-amino-2-(2-hydroxyethylamino)phenylcarbamoyl]methyl}-1,4-dimethylpiperazin-1-ium chloride;

1-[2-(4-aminophenylamino)ethyl]-3-methyl-3H-imidazol-1-ium bromide;

1-[3-(2,5-diaminophenoxy)propyl]-3-methyl-3H-imidazol-1-ium chloride;

3-[3-(4-aminophenylamino)propyl]-1-methyl-3H-imidazol-1-ium chloride;

3-[3-(4-amino-3-methylphenylamino)propyl]-1-methyl-3H-imidazol-1-ium chloride;

3-[3-(4-amino-2-methylphenylamino)propyl]-1-methyl-3H-imidazol-1-ium chloride;

3-[3-(4-amino-2-fluorophenylamino)propyl]-1-methyl-3H-imidazol-1-ium chloride;

3-[3-(4-amino-2-cyanophenylamino)propyl]-1-methyl-3H-imidazol-1-ium chloride;

1-[2-(4-amino-2-methoxyphenylamino)ethyl]-3-methyl-3H-imidazol-1-ium chloride;

1-(5-amino-2-hydroxybenzyl)-3-methyl-3H-imidazol-1-ium chloride;

1-(5-amino-2-hydroxybenzyl)-2-methyl-2H-pyrazol-1-ium chloride;

1-[2-(2,5-diaminophenyl)ethyl]-3-methyl-3H-imidazol-1-ium chloride;

3-[2-(2,5-diaminophenyl)ethyl]-1-methyl-3H-imidazol-1-ium chloride;

1-{2-[(4-aminophenyl)ethylamino]ethyl}-3-methyl-3H-imidazol-1-ium chloride;

N,N-bis[2-(3-methyl-3H-imidazol-1-ium)ethyl]-4-aminoaniline dichloride;

3-[2-(4-aminophenylamino)butyl]-1-methyl-3H-imidazol-1-ium chloride;
1-{[5-amino-2-(2-hydroxyethylamino)phenylcarbamoyl]methyl}-3-methyl-3H-imidazol-1-ium chloride;
4-[2-(2,5-diaminophenoxy)ethyl]-1,3-dimethyl-3H-imidazol-1-ium bromide;
2-(2,5-diaminophenoxymethyl)-1,3-dimethyl-3H-imidazol-1-ium chloride;
4-[3-(4-aminophenylamino)propyl]-1,3-dimethyl-3H-imidazol-1-ium chloride;
4-[3-(4-amino-3-methylphenylamino)propyl]-1,3-dimethyl-3H-imidazol-1-ium chloride;
4-[(2,5-diaminophenylcarbamoyl)methyl]-1,3-dimethyl-3H-imidazol-1-ium chloride;
4-{2-[2-(2-amino-5-hydroxyphenyl)acetylamino]ethyl}-1,3-dimethyl-3H-imidazol-1-ium chloride;
4-[(5-amino-2-hydroxybenzylcarbamoyl)methyl]-1,3-dimethyl-3H-imidazol-1-ium chloride; and the addition salts thereof.

15. The composition according to claim 14, wherein the monobenzenic para-phenylenediamines and monobenzenic para-aminophenols are chosen from:
[2-(2,5-diaminophenoxy)ethyl]diethylmethylammonium chloride;
N,N-bis(trimethylammoniumpropyl)-4-aminoaniline chloride;
[4-(4-aminophenylamino)pentyl]diethylmethylammonium chloride;
[2-(4-aminophenylamino)ethyl]diethylmethylammonium chloride;
{2-[(4-aminophenyl)methylamino]ethyl}trimethylammonium chloride;
[3-(4-aminophenylamino)propyl]trimethylammonium chloride;
[4-(4-aminophenylamino)pentyl]diethyl-(2-hydroxyethyl)ammonium chloride;
3-[3-(4-aminophenylamino)propyl]-1-methyl-3H-imidazol-1-ium chloride;
1-[3-(2,5-diaminophenoxy)propyl]-3-methyl-3H-imidazol-1-ium chloride;
3-[3-(4-amino-3-methylphenylamino)propyl]-1-methyl-3H-imidazol-1-ium chloride;
3-[3-(4-amino-2-methylphenylamino)propyl]-1-methyl-3H-imidazol-1-ium chloride;
1-[2-(4-amino-2-methoxyphenylamino)ethyl]-3-methyl-3H-imidazol-1-ium chloride;
3-[3-(4-amino-2-fluorophenylamino)propyl]-1-methyl-3H-imidazol-1-ium chloride;
3-[3-(4-amino-2-cyanophenylamino)propyl]-1-methyl-3H-imidazol-1-ium chloride and the addition salts thereof.

16. The composition according to claim 14, wherein the monobenzenic para-phenylenediamines are 1,3,-bis[3-(2,5,-diaminophenoxy)propyl]-3H-imidazol-1-ium monochloride tetrahydrochloride monohydrate.

17. The composition according to claim 13, wherein the dibenzenic para-phenylenediamines and dibenzenic para-aminophenols are chosen from:
1,3-bis-1{3{3'[(4"-amino-3"-methylaniline)-N-propyl]}-3H-imidazol-1-ium}propane dichloride;
1,3-bis-1{3{3'[(4"-amino-2"-methylaniline)-N-propyl]}-3H-imidazol-1-ium}propane dichloride;
1,3-bis-1{3{3'[(4"-aminoaniline)-N-propyl]}-3H-imidazol-1-ium}propane dichloride;
1,3-bis-1{3{3'[(4"-aminoaniline)-N-propyl]}-3H-imidazol-1-ium}-2-propanol dichloride;
$N_1,N_3$-bis-[3-N-(4'-aminoaniline)propyl]-1,1,3,3-tetramethyl-1,3-diammoniumpropane dibromide;
1,4-bis-1{3[3-(2,5-diaminophenoxy)propyl]-3H-imidazol-1-ium)butane dichloride;
1,3-bis[3-(2,5-diaminophenoxy)propyl]-3H-imidazol-1-ium monochloride;
$N_1,N_4$-bis-[3-N-methyl-N-(4'-aminoaniline)ethyl]-1,1,4,4-tetramethyl-1,3-diammoniumpropane dibromide;
1,4-bis-1-[3-(5-amino-2-hydroxybenzyl)-3H-imidazol-1-ium]butane dichloride;
1,3-bis-{[2-(4-aminoaniline)propyl]-1,1,3,3-tetramethyldiammoniumpropane dibromide;
1,3-bis-{[4-(4-aminoaniline)pentyl]-1,1,3,3-tetramethyldiammoniumpropane dichloride;
[4-(4-aminophenylamino)pentyl]-(5-amino-2-hydroxybenzyl)diethylammonium monochloride;
[2-(4-aminophenylamino)propyl]-(5-amino-2-hydroxybenzyl)dimethylammonium monochloride;
1,3-bis-1-{3-[3-(2,5-diaminophenoxy)propyl]-3H-imidazol-1-ium}propane dichloride;
1,3-bis-1{3'{3'[(4"-aminoaniline)-N-propyl]}-3H-imidazol-1-ium}propane dichloride;
1,3-bis-1{4{4'(4-[3-(4"-aminophenylamino)propyl]}-1,3-dimethyl-3H-imidazol-1-ium}propane dichloride;
1,3-bis-1{4{4'(4-[3-(4"-amino-2"-methylaniline)propyl]}-1,3-dimethyl-3H-imidazol-1-ium}propane dichloride;
4-[2-(2,5-diaminophenoxy)ethyl]-3-[3-(2,5-diaminophenoxy)propyl]-1-methyl-3-imidazol-1-ium monochloride;
4-[2-(2,5-diaminophenoxy)ethyl]-1-[3-(2,5-diaminophenoxy)propyl]-3-methyl-3-imidazol-1-ium monochloride;
and the addition salts thereof.

18. The composition according to claim 17, wherein the dibenzenic para-phenylenediamines and dibenzenic para-aminophenols are chosen from:
1,3-bis-1{3{3'[(4"-aminoaniline)-N-propyl]}-3H-imidazol-1-ium}propane dichloride;
1,3-bis[3-(2,5-diaminophenoxy)propyl]-3H-imidazol-1-ium monochloride;
$N_1,N_4$-bis-[3-N-methyl-N-(4'-aminoaniline)ethyl]-1,1,4,4-tetramethyl-1,3-diammoniumpropane dibromide;
1,4-bis-1-[3-(5-amino-2-hydroxybenzyl)-3H-imidazol-1-ium]butane dichloride;
1,3-bis-1{3{3'[(4"-aminoaniline)-N-propyl]}-3H-imidazol-1-ium}propane dichloride;
and the addition salts thereof.

19. The composition according to claim 13, wherein the monobenzenic ortho-phenylenediamines are chosen from:
{2-[2-aminophenylamino]ethyl}trimethylammonium monochloride;
[2-(2-amino-5-chlorophenylamino)ethyl]trimethylammonium monochloride;
[2-(2-amino-6-chlorophenylamino)ethyl]trimethylammonium monochloride;
[2-(2-amino-4-chlorophenylamino)ethyl]trimethylammonium monochloride;
{2-[2-amino-4-chloro-5-(2-hydroxyethoxy)phenylamino]ethyl}trimethylammonium monochloride;

[2-(2-amino-5-methoxyphenylamino)ethyl] trimethylammonium monochloride;

[2-(2-aminophenylamino)ethyl]-(2-hydroxyethyl) dimethylammonium monobromide;

4-[2-(2-aminophenylamino)ethyl]-4-methylmorpholin-4-ium monochloride;

1-[2-(2-aminophenylamino)ethyl]-1-ethylpiperidinium monochloride;

1-[2-(2-aminophenylamino)ethyl]-1,4-dimethylpiperazin-1-ium monochloride;

4-[2-(1-methylpiperidinium)ethoxy]-N2-[2-(1-methylpiperidinium)ethyl]benzene-1,2-diamine dichloride;

1-[2-(2-amino-5-methylsulphanylphenylamino)ethyl]-1-methylpiperidinium monochloride;

1-[2-(2-aminophenylamino)ethyl]-1-methylpyrrolidinium monochloride;

[3-(2-aminophenylamino)propyl] diethylmethylammonium monochloride;

N,N'-bis-[2-(1-methylpiperidinium)ethyl]benzene-1,2-diamine dichloride;

[2-(2-amino-4-methylphenylamino)ethyl]trimethyl [lacuna] monochloride;

3-[3-(2-aminophenylamino)propyl]-1-methyl-3H-imidazol-1-ium monochloride;

3-[2-(2-aminophenylamino)ethyl]-1-methyl-3H-imidazol-1-ium monochloride;

4-[2-(1-methyl-3H-imidazol-1-ium)ethoxy]-N-2-[2-(1-methyl-3H-imidazol-1-ium)ethyl]benzene-1,2-diamine dichloride;

3-[2-(2-amino-4-methylphenylamino)ethyl]-1-ethyl-3H-imidazol-1-ium monochloride;

3-[3-(2-aminophenylamino)propyl]-1-(3-trimethylammonium-2-hydroxypropyl)-3H-imidazol-1-ium dichloride;

3-[3-(2-aminophenylamino)propyl]-1-(2-hydroxyethyl)-3H-imidazol-1-ium monobromide;

3-{[2-(2-aminophenylamino)ethylcarbamoyl]methyl}-1-methyl-3H-imidazol-1-ium monochloride;

1-[2-(2-amino-4-chlorophenylamino)ethyl]pyridinium monochloride;

3-[2-(2-amino-5-methoxyphenylamino)ethyl]-1-methyl-3H-imidazol-1-ium monochloride;

3-[2-(2-amino-5-methylsulphanylphenylamino)ethyl]-1-methyl-3H-imidazol-1-ium monochloride;

and the addition salts thereof.

20. The composition according to claim 19, wherein the monobenzenic ortho-phenylenediamines are chosen from:

{2-[2-aminophenylamino]ethyl}trimethylammonium chloride;

3-[3-(2-aminophenylamino)propyl]-1-methyl-3H-imidazol-1-ium chloride;

and the addition salts thereof.

21. The composition according to claim 13, wherein the dibenzenic ortho-phenylenediamines are chosen from:

1,3-bis-{3-{3-[(2-aminoaniline)-N-propyl]}-3H-imidazol-1-ium}propane dibromide;

N$_1$,N$_3$-bis-[3-N-(2-aminoaniline)propyl]-1,1,3,3-tetramethyl-1,3-diammoniumpropane dibromide;

1,4-bis-{3-{2-[(2-aminoaniline)-N-ethyl]}-3H-imidazol-1-ium}butane dichloride;

1-[2-(2-aminoaniline)ethyl]-3-[3-(2-aminoaniline)propyl]-3H-imidazol-1-ium monochloride;

and the addition salts thereof.

22. The composition according to claim 21, wherein the dibenzenic ortho-phenylenediamines are chosen from:

1,3-bis-1-{3-{3-[(2-aminoaniline)-N-propyl]}-3H-imidazol-1-ium}propane dibromide;

N$_1$,N$_3$-bis-[3-N-(2-aminoaniline)propyl]-1,1,3,3-tetramethyl-1,3-diammoniumpropane dibromide;

and the addition salts thereof.

23. The composition according to claim 13, wherein the heterocyclic oxidation bases of the pyrazole type are chosen from:

[3-(4-amino-2,5-dimethyl-2H-pyrazol-3-ylamino)propyl] trimethylammonium chloride;

[3-(4-amino-2,5-dimethyl-2H-pyrazol-3-ylamino)propyl]-(2-hydroxyethyl)dimethylammonium chloride;

3-[3-(4-amino-2,5-dimethyl-2H-pyrazol-3-ylamino)propyl]-1-(2-hydroxyethyl)-3H-imidazol-1-ium chloride;

3-[(4-amino-2H-pyrazol-3-ylcarbamoyl)methyl]-1-methyl-3H-imidazol-1-ium chloride;

3-[2-(4,5-diamino-3-methylpyrazol-1-yl)ethyl]-1-methyl-3H-imidazol-1-ium chloride;

3-[2-(4,5-diaminopyrazol-1-yl)ethyl]-1-methyl-3H-imidazol-1-ium chloride;

[2-(4,5-diamino-3-methylpyrazol-1-yl)ethyl] trimethylammonium chloride;

[2-(4,5-diaminopyrazol-1-yl)ethyl]trimethylammonium chloride;

[2-(4-amino-5-hydroxypyrazol-1-yl)ethyl] trimethylammonium chloride;

[2-(4-amino-5-hydroxy-3-methylpyrazol-1-yl)ethyl] trimethylammonium chloride;

3-[2-(4-amino-5-hydroxy-3-methylpyrazol-1-yl)ethyl]-1-methyl-3H-imidazol-1-ium chloride;

3-[2-(4-amino-5-hydroxypyrazol-1-yl)ethyl]-1-methyl-3H-imidazol-1-ium chloride;

3-[2-(4,5-diamino-1-methyl-1H-pyrazol-3-yl)ethyl]-1-methyl-3H-imidazol-1-ium chloride;

and the addition salts thereof, and the possible tautomeric forms thereof.

24. The composition according to claim 23, wherein the heterocyclic oxidation bases of the pyrazole type are chosen from:

[3-(4-amino-2,5-dimethyl-2H-pyrazol-3-ylamino)propyl] trimethylammonium chloride;

[3-(4-amino-2,5-dimethyl-2H-pyrazol-3-ylamino)propyl]-(2-hydroxyethyl)dimethylammonium chloride;

3-[3-(4-amino-2,5-dimethyl-2H-pyrazol-3-ylamino)propyl]-1-(2-hydroxyethyl)-3H-imidazol-1-ium chloride;

3-[(4-amino-2H-pyrazol-3-ylcarbamoyl)methyl]-1-methyl-3H-imidazol-1-ium chloride;

3-[2-(4,5-diamino-3-methylpyrazol-1-yl)ethyl]-1-methyl-3H-imidazol-1-ium chloride;

3-[2-(4,5-diamino-1-methyl-1H-pyrazol-3-yl)ethyl]-1-methyl-3H-imidazol-1-ium chloride, and the addition salts thereof, and the possible tautomeric forms thereof.

25. The composition according to claim 13, wherein the heterocyclic oxidation bases of the pyrazolo[1,5-a] pyrimidine type are chosen from:

1-[3-(3-amino-5,6-dimethylpyrazolo[1,5-a]pyrimidin-7-ylamino)propyl]-3-methyl-3H-imidazol-1-ium monobromide, 3-[3-(3-amino-5-methylpyrazolo[1,5-a]pyrimidin-7-ylamino)propyl]-1-(2-hydroxyethyl)-3H-imidazol-1-ium chloride, 3-[(3-aminopyrazolo[1,5-a]pyrimidin-7-ylcarbamoyl)methyl]-1-methyl-3H-imidazol-1-ium chloride, 3-(3-amino-7-hydroxy-5-methylpyrazolo[1,5-a]pyrimidin-6-ylmethyl)-1-methylpyridinium methyl sulphate, 3-(3-amino-7-hydroxy-5-methylpyrazolo[1,5-a]pyrimidin-6-ylmethyl)-1-(2-hydroxyethyl)pyridinium chloride, 2-[(3-aminopyrazolo[1,5-a]pyrimidin-7-ylamino)methyl]-1,3-dimethyl-3H-imidazol-1-ium methyl sulphate, 3-[(3-aminopyrazolo[1,5-a]pyrimidin-7-ylamino)methyl]-1-methylpyridinium methyl sulphate, 3-[(3-aminopyrazolo[1,5-a]pyrimidin-7-ylamino)methyl]-1-methylpyridinium methyl sulphate, 2-(3,7-diamino-5-methylpyrazolo[1,5-a]pyrimidin-6-ylmethyl]-1,3-dimethyl-3H-imidazol-1-ium methyl sulphate, 2-(3-amino-7-hydroxy-5-methylpyrazolo[1,5-a]pyrimidin-6-ylmethyl)-1,3-dimethyl-3H-imidazol-1-ium methyl sulphate, 2-(3,7-diaminopyrazolo[1,5-a]pyrimidin-2-yl)-1-methylpyridinium methyl sulphate,

[3-(3-amino-5-methylpyrazolo[1,5-a]pyrimidin-7-ylamino)propyl]trimethylammonium chloride,

[3-(3-amino-5-methylpyrazolo[1,5-a]pyrimidin-7-ylamino)propyl]trimethylammonium methyl sulphate, 1-[3-(3-amino-5-methylpyrazolo[1,5-a]pyrimidin-7-ylamino)propyl]-1-methylpiperidinium chloride, 1-[3-(3-amino-5-methylpyrazolo[1,5-a]pyrimidin-7-ylamino)propyl]-1-methylpiperidinium methyl sulphate, 4-[3-(3-amino-5-methylpyrazolo[1,5-a]pyrimidin-7-ylamino)propyl]-4-methylmorpholin-4-ium chloride, 4-[3-(3-amino-5-methylpyrazolo[1,5-a]pyrimidin-7-ylamino)propyl]-4-methylmorpholin-4-ium methyl sulphate, and the addition salts thereof.

26. The composition according to claim 25, wherein the heterocyclic oxidation bases of the pyrazolo[1,5-a]pyrimidine type are chosen from:

1-[3-(3-amino-5,6-dimethylpyrazolo[1,5-a]pyrimidin-7-ylamino)propyl]-3-methyl-3H-imidazol-1-ium monobromide, 3-[3-(3-amino-5-methylpyrazolo[1,5-a]pyrimidin-7-ylamino)propyl]-1-(2-hydroxyethyl)-3H-imidazol-1-ium chloride, 3-(3-amino-7-hydroxy-5-methylpyrazolo[1,5-a]pyrimidin-6-ylmethyl)-1-methylpyridinium methyl sulphate, 3-(3-amino-7-hydroxy-5-methylpyrazolo[1,5-a]pyrimidin-6-ylmethyl)-1-(2-hydroxyethyl)pyridinium chloride, 3-(3-amino-7-hydroxy-5-methylpyrazolo[1,5-a]pyrimidin-6-ylmethyl)-1-methylpyridinium chloride, 4-[3-(3-amino-5-methylpyrazolo[1,5-a]pyrimidin-7-ylamino)propyl]-4-methylmorpholin-4-ium chloride, 4-[3-(3-amino-5-methylpyrazolo[1,5-a]pyrimidin-7-ylamino)propyl]-4-methylmorpholin-4-ium methyl sulphate, and the addition salts thereof.

27. The composition according to claim 1, wherein the at least one coupler is chosen from meta-phenylenediamines, meta-aminophenols, meta-diphenols, naphthalenic couplers and heterocyclic couplers, and the addition salts thereof.

28. The composition according to claim 27, wherein the at least one coupler is present in an amount ranging from 0.001% to 10% by weight, relative to the total weight of the dye composition.

29. The composition according to claim 1, further comprising at least one additional non-cationic oxidation base chosen from para-phenylenediamines, bis(phenyl)alkylenediamines, para-aminophenols, ortho-aminophenols and heterocyclic bases, other than the at least one first oxidation base, and the addition salts thereof.

30. The composition according to claim 1, wherein the amount of each of said at least one first oxidation base included in the composition ranges from 0.001% to 10% by weight, relative to the total weight of the dye composition.

31. The composition according to claim 1, further comprising at least one oxidizing agent.

32. The composition according to claim 31, wherein the at least one oxidizing agent is chosen from hydrogen peroxide, urea peroxide, alkali metal bromates, persalts, peracids and oxidase enzymes.

33. The composition according to claim 1, further comprising at least one direct dye chosen from nitrobenzene direct dyes, azo direct dyes, and methine direct dyes.

34. The composition according to claim 33, wherein the at least one direct dye is nonionic, anionic, or cationic in nature.

35. A process for oxidation dyeing of keratin fibres, comprising applying to the keratin fibres at least one dye composition comprising, in a medium suitable for dyeing, at least one first oxidation base chosen from 4,5-diaminopyrazole derivatives of formula (I) and the addition salts thereof,

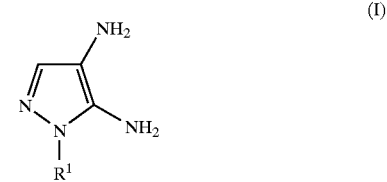

(I)

wherein $R^1$ is chosen from $C_1$–$C_6$ alkyl radicals substituted with at least one radical chosen from $OR^2$ radicals wherein $R^2$ is chosen from $C_1$–$C_6$ alkyl radicals;

at least one second cationic oxidation base chosen from monobenzenic, dibenzenic and heterocyclic oxidation bases, and the addition salts thereof, wherein said at least one second cationic oxidation base comprises at least one cationic group Z chosen from aliphatic chains optionally bearing at least one ring chosen from saturated and unsaturated rings; wherein said at least one cationic group Z is linked directly to at least one benzenic ring or to at least one heterocycle of said at least one second cationic oxidation base or linked to at least one amine functional group borne by said at least one benzenic ring or said at least one heterocycle; and at least one coupler;

and at least one oxidizing agent.

36. The process according to claim 35, wherein the at least one oxidizing agent is chosen from hydrogen peroxide, urea peroxide, alkali metal bromates, persalts, peracids and oxidase enzymes.

37. The process according to claim 35, comprising mixing, at the time of use, the at least one oxidizing agent with the at least one dye composition.

38. A process for oxidation dyeing of keratin fibres, comprising applying to the keratin fibres at least one oxidizing composition comprising, in a medium suitable for dyeing, at least one oxidizing agent, simultaneously or sequentially to at least one dye composition comprising, in a medium suitable for dyeing, at least one first oxidation base chosen from 4,5-diaminopyrazole derivatives of formula (I) and the addition salts thereof,

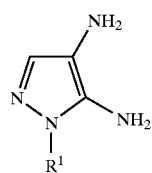

(I)

wherein $R^1$ is chosen from $C_1$–$C_6$ alkyl radicals substituted with at least one radical chosen from $OR^2$ radicals wherein $R^2$ is chosen from $C_1$–$C_6$ alkyl radicals;

at least one second cationic oxidation base chosen from monobenzenic, dibenzenic and heterocyclic oxidation bases, and the addition salts thereof, wherein said at least one second cationic oxidation base comprises at least one cationic group Z chosen from aliphatic chains optionally bearing at least one ring chosen from saturated and unsaturated rings; wherein said at least one cationic group Z is linked directly to at least one benzenic ring or to at least one heterocycle of said at least one second cationic oxidation base or linked to at least one amine functional group borne by said at least one benzenic ring or said at least one heterocycle; and at least one coupler.

39. A multi-compartment kit or device comprising a first compartment comprising at least one dyeing composition comprising, in a medium suitable for dyeing, at least one first oxidation base chosen from 4,5-diaminopyrazole derivatives of formula (I) and the addition salts thereof,

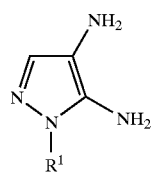

(I)

wherein $R^1$ is chosen from $C_1$–$C_6$ alkyl radicals substituted with at least one radical chosen from $OR^2$ radicals wherein $R^2$ is chosen from $C_1$–$C_6$ alkyl radicals;

at least one second cationic oxidation base chosen from monobenzenic, dibenzenic and heterocyclic oxidation bases, and the addition salts thereof, wherein said at least one second cationic oxidation base comprises at least one cationic group Z chosen from aliphatic chains optionally bearing at least one ring chosen from saturated and unsaturated rings; wherein said at least one cationic group Z is linked directly to at least one benzenic ring or to at least one heterocycle of said at least one second cationic oxidation base or linked to at least one amine functional group borne by said at least one benzenic ring or said at least one heterocycle; and at least one coupler;

and a second compartment comprising at least one oxidizing composition.

40. A process for dyeing keratin fibres, comprising applying to keratin fibres a dye composition comprising, in a medium suitable for dyeing, at least one first oxidation base chosen from 4,5-diaminopyrazole derivatives of formula (I) and the addition salts thereof,

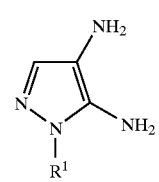

(I)

wherein $R^1$ is chosen from $C_1$–$C_6$ alkyl radicals substituted with at least one radical chosen from $OR^2$ radicals wherein $R^2$ is chosen from $C_1$–$C_6$ alkyl radicals;

at least one second cationic oxidation base chosen from monobenzenic, dibenzenic and heterocyclic oxidation bases, and the addition salts thereof, wherein said at least one second cationic oxidation base comprises at least one cationic group Z chosen from aliphatic chains optionally bearing at least one ring chosen from saturated and unsaturated rings; wherein said at least one cationic group Z is linked directly to at least one benzenic ring or to at least one heterocycle of said at least one second cationic oxidation base or linked to at least one amine functional group borne by said at least one benzenic ring or said at least one heterocycle; and at least one coupler.

41. A process for manufacturing a dye composition comprising including in the dye composition at least one first oxidation base chosen from 4,5-diaminopyrazole derivatives of formula (I) and the addition salts thereof,

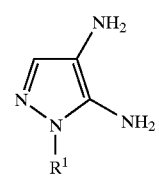

(I)

wherein $R^1$ is chosen from $C_1$–$C_6$ alkyl radicals substituted with at least one radical chosen from $OR^2$ radicals wherein $R^2$ is chosen from $C_1$–$C_6$ alkyl radicals;

at least one second cationic oxidation base chosen from monobenzenic, dibenzenic and heterocyclic oxidation bases, and the addition salts thereof, wherein said at least one second cationic oxidation base comprises at least one cationic group Z chosen from aliphatic chains optionally bearing at least one ring chosen from saturated and unsaturated rings; wherein said at least one cationic group Z is linked directly to at least one benzenic ring or to at least one heterocycle of said at least one second cationic oxidation base or linked to at least one amine functional group borne by said at least one benzenic ring or said at least one heterocycle; and at least one coupler.

* * * * *